(12) United States Patent
Stenger (10) Patent No.: US 8,034,107 B2
(45) Date of Patent: Oct. 11, 2011

(54) ACCOMMODATING INTRAOCULAR LENS

(76) Inventor: Donald C. Stenger, San Clemente, CA (US)

( * ) Notice: Subject to any disclaimer, the term of this patent is extended or adjusted under 35 U.S.C. 154(b) by 526 days.

(21) Appl. No.: 11/469,300

(22) Filed: Aug. 31, 2006

(65) Prior Publication Data

US 2007/0156236 A1    Jul. 5, 2007

Related U.S. Application Data (60) Provisional application No. 60/713,943, filed on Sep. 1, 2005.

(51) Int. Cl.
    *A61F 2/16* (2006.01)
(52) U.S. Cl. .................. 623/6.34; 623/6.37; 623/6.4
(58) Field of Classification Search ............. 623/6.13, 623/6.21, 6.38, 6.39, 6.4, 6.41, 6.42, 6.37, 623/6.32–6.34
    See application file for complete search history.

(56) References Cited

U.S. PATENT DOCUMENTS

| | | | |
|---|---|---|---|
| 4,285,072 A | 8/1981 | Morcher et al. | |
| 4,676,792 A | 6/1987 | Praeger | |
| 4,710,195 A | 12/1987 | Giovinazzo | |
| 4,994,080 A | 2/1991 | Shepard | |
| 5,133,747 A | 7/1992 | Feaster | |
| 5,275,623 A | 1/1994 | Sarfarazi | |
| 5,376,116 A * | 12/1994 | Poler | 623/6.16 |
| 5,476,514 A | 12/1995 | Cumming | |
| 5,496,366 A | 3/1996 | Cumming | |
| 5,674,282 A | 10/1997 | Cumming | |
| 5,928,282 A | 7/1999 | Nigam | |
| 6,015,435 A | 1/2000 | Valunin et al. | |
| 6,083,261 A | 7/2000 | Callahan et al. | |
| 6,197,059 B1 | 3/2001 | Cumming | |
| 6,241,777 B1 | 6/2001 | Kellan | |
| 6,261,321 B1 | 7/2001 | Kellan | |
| 6,302,911 B1 | 10/2001 | Hanna | |
| 6,749,634 B2 * | 6/2004 | Hanna | 623/6.37 |
| 7,125,422 B2 | 10/2006 | Woods et al. | |
| 7,462,194 B1 * | 12/2008 | Blake | 623/6.46 |
| 2002/0002404 A1 | 1/2002 | Sarfarazi | |
| 2002/0128710 A1 * | 9/2002 | Eggleston | 623/6.22 |
| 2003/0060878 A1 | 3/2003 | Shadduck | |
| 2003/0147046 A1 | 8/2003 | Shadduck | |
| 2005/0119740 A1 | 6/2005 | Esch et al. | |
| 2005/0209692 A1 * | 9/2005 | Zhang | 623/6.34 |
| 2006/0047339 A1 * | 3/2006 | Brown | 623/6.13 |
| 2007/0027538 A1 * | 2/2007 | Aharoni et al. | 623/6.12 |

FOREIGN PATENT DOCUMENTS

| | | |
|---|---|---|
| WO | 00/66037 | 11/2000 |
| WO | 01/34067 | 5/2001 |

* cited by examiner

*Primary Examiner* — William H. Matthews
(74) *Attorney, Agent, or Firm* — Hani Z. Sayed; Rutan & Tucker, LLP (57) ABSTRACT

An Accommodating Intraocular Lens (AIOL) is disclosed herein, that is comprised of a flexible optic and a flexible haptic rim that conforms to the human eye capsule. The spherical or custom shape of the optic is engineered to be maintained during accommodation through the mechanical/optic design of the implant and the interaction between the implant and the naturally occurring position and actuating forces applied through ciliary muscle/zonules/and capsule as the brain senses the need to increase the diopter change or magnification when an object of fixation approaches the eye. The axial relocation or position of the AIOL may also be further adjusted anatomically to further improve the affect needed to achieve improved accommodation. Optionally, the accommodating intraocular lens is foldable or injectable for delivery of the lens into the eye.

19 Claims, 4 Drawing Sheets

ACCOMMODATING INTRAOCULAR LENS

PRIORITY DATA

This application claims priority to an earlier filed U.S. Provisional Patent, Ser. No. 60/713,943 filed on Sep. 1, 2005.

FIELD OF THE INVENTION

This invention relates generally to the field of Intraocular lenses (IOL) and, more particularly, to an accommodative IOL (AIOL).

BACKGROUND OF THE INVENTION

The human eye provides vision by transmitting light through a clear outer portion, the cornea, and the eye focuses the image onto the retina by way of a crystalline lens. The image quality depends on many optical factors including the size and shape of the eye, and the transparency of the cornea and lens.

When age or disease causes the lens to become less transparent, vision deteriorates because of the reduced light which can be transmitted to the retina. This medical condition or deficiency of the lens of the eye is medically known as a cataract. To treat this medical condition the lens is typically surgically removed and replaced by an artificial intraocular lens (IOL).

In the United States, the majority of cataractous lenses are surgically removed using a procedure called phacoemulsification. During this procedure, an opening, or capsulorhexis, approximately 4 mm in diameter is made in the anterior capsule of the crystalline lens, and a small diameter phacoemulsification cutting tip is inserted into the cataractous lens and the simultaneous ultrasonic motion and aspiration suction removes this cataractous lens without damage to the surrounding capsule. An artificial lens is then implanted to replace the natural lens; however, this lens typically, in the past, has been what is called a monofocal lens with just one focal length. Having only one focal length requires one to use reading glasses because that patient can no longer accommodate naturally to magnify his near vision.

Examples of implatable artificial intraocular lenses include various design configurations. Generally, the lenses are attached in some manner within the eye, usually by sutures to the iris, or some other supporting means, such as arms, or haptics, extending from the optical lens portion of the intraocular lens.

U.S. Pat. No. 4,053,953 describes an artificial intraocular lens for the aphakic eye. The lens is secured in the posterior chamber by a system of posts that protrude through the iris attached to retaining rings.

U.S. Pat. No. 6,015,435 describes a self-centering phakic intraocular lens inserted in to the posterior chamber lens for the correction of myopia, hyperopia, astigmatism, and presbyopia. Haptic bodies are attached to the optical body and extend outward from tangent points at the edge of lens in at least two generally opposite directions. Protruding surfaces protrude into pupil such that the iris interferes slightly with lens movement and provides the centering force to keep lens in place.

U.S. Pat. No. 4,710,195 describes a posterior chamber lens, particularly adapted for patients with glaucoma and cataracts. Two haptics are connected to the optic body at its edge. The haptics are offset from the other by 180 degrees and extend circumferentially around the edge of the optic portion. The haptics end in enlarged "blocking segments".

U.S. Pat. No. 4,676,792 describes an artificial intraocular lens device implantable in the anterior chamber of the eye (in front of the iris) for treating myopia. The optic body has three or four "J" shaped haptics that terminate with solid footplates to anchor the lens. In one embodiment, haptics are positioned circumferentially around the edge of the optic body approximately 90 degrees apart. The haptics are grouped in pairs so that each pair is oriented such that the respective curved surfaces of solid footplates face each other.

U.S. Pat. No. 5,133,747 describes an intraocular lens device that is partially or completely within the anterior capsular surface of the human crystalline lens. In one embodiment, the optic body has asymmetrical haptics extending outwardly from opposite sides of the periphery of the optic body. In one embodiment, "J" shaped haptics extend from the periphery of the optic body in a manner that encircles the optic body. In another configuration, the haptics extend tangentially away from body, then reverse direction, giving the device an overall "S" shape with the lens at the center portion of the S. The device is secured in place with an adhesive.

U.S. Pat. No. 5,928,282 describes a refractive intraocular lens for implantation into the anterior chamber. The lens body has elongated, ovoid-disc shaped haptics extending from its peripheral edge.

U.S. Pat. No. 4,994,080 describes optical lens devices having an optical body with multiple perforations and two J shaped haptics that terminate in footplates.

U.S. Pat. No. 6,083,261 describes an intraocular lens having crossed haptics for implantation into either phakic or aphakic eye.

U.S. Pat. No. 4,285,072 describes closed loop haptics on an intraocular lens. When positioned in the eye, the circular arched haptics without footplates extend rearward from the optic body, then angle sideways to allow the arch to rest in the angle to keep the lens in place. This design proved to be physiologically unsuitable for use.

U.S. Pat. No. 5,275,623 (Sarfarzi) describes an elliptical accommodative intraocular lens having dual lens fixed optics.

WIPO Publication No. 00/66037 (Glick et al.) describes a dual fixed optic intraocular lens.

WO 01/34067 A1 (Bandhauer, et al) describes an accommodating intraocular lens system with specific flexibility characteristics to facilitate axial displacement of a positive fixed optic portion.

U.S. Pat. Nos. 6,197,059; 5,674,282; 5,496,366; and 5,476,514 (all by Cummings) describe an accommodating intraocular lens having a central optic and two flexible haptics that allow forward and backward fixed optic motion in reaction to ciliary muscle movement.

Similar designs are described in U.S. Pat. No. 6,302,911 B1 (Hanna), U.S. Pat. Nos. 6,261,321 D1 and 6,241,777 B1 (both to Kellan).

According to U.S. Pat. Nos. 6,197,059, 5,674,282, 5,496,366 and 5,476,514, the eye must be paralyzed for one to two weeks in order for capsular fibrosis to entrap the lens thereby provide or a rigid association between this type of lens and the capsular bag.

U.S. Pat. Pub. No. 2002/0002404 A1 (Sarfarazi) describes an open chamber, elliptical, accommodating intraocular lens system.

U.S. Pat. No. 2005/0119741 A1 (Esch et al.) describes a fluid filled/piston driven accommodating intraocular deformable optic lens.

U.S. Pat. Pub. No. 2003/10147046 A1 (Shadduck) describes an intraocular lens capable to create highly localized surface corrections in the lens to correct higher order aberrations.

U.S. Pat. Pub. No. 2003/0060878 A1 (Shadduck) describes an intraocular lens capable of cooperating with an external RE or light source to expose a charge to a charge-carrying fluid within the interior chamber.

This and all other referenced patents and applications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

As the human lens ages, it becomes harder, usually well before becoming cataractous, and is less able to return to it's relaxed, smaller optical radius shape with a smaller equatorial diameter that is required for near vision as the ciliary muscle tightens or contracts when the brain activates this muscle to magnify an image that one desires to see up close. This lens hardening over several years makes it impossible for the lens to deform as needed to focus on near objects. This medical condition is known as presbyopia. Presbyopia affects nearly all adults over the age of 45 to 50. To treat presbyopia, the lens could be surgical removed and replaced by an artificial accommodating intraocular lens (AIOL).

Therefore, a need exists for an intraocular lens that has accommodating effects for the patient. Additionally, a need exists for an intraocular lens that may flex to allow for natural physical and neural eye anatomy.

SUMMARY OF THE INVENTION

The present invention relates to an Accommodating Intraocular Lens (AIOL). The AIOL herein described may have a flexible optic and a flexible haptic rim that conforms to the human eye capsule allowing for increased visibility by a patient needing an Accommodating Intraocular Lens. The spherical or custom shape of the optic may be engineered to maintain its shape during accommodation through the mechanical/optic design of the implant and the interaction between the implant and the naturally occurring position and actuating forces applied through ciliary muscle and capsule as the brain senses the need to increase the diopter change. Additionally, when the brain senses the need for magnification of an object approaching the eye, the naturally occurring forces applied by a ciliary muscle on the haptic may cause change in the lens. The axial relocation or position of the AIOL may also be further adjusted anatomically to further improve the affect needed to achieve improved accommodation. In an exemplary embodiment, the accommodating intraocular lens is foldable or injectable for delivery of the lens into the eye.

To this end, in an exemplary embodiment of the present invention, an accommodating intraocular lens device is disclosed. The device has a conforming lens for insertion into the capsular bag of the eye and an actuating haptic wherein the conforming lens is detachably connected to the actuating haptic.

In an exemplary embodiment, the device has a conforming lens that may be solid and thin, with a thin surface film filled with a soft inner core.

In an exemplary embodiment, the device may have a conforming lens having an interior is a solid.

In an exemplary embodiment, the device may have a conforming lens having an interior portion wherein the interior portion is liquid.

In an exemplary embodiment, the device may have a conforming lens having an interior portion wherein the interior portion is filled with a gaseous solution.

In an exemplary embodiment, the device may have a conforming lens that is convexed anteriorly with a planar posterior surface.

In an exemplary embodiment, the device may have a lens that is made up of a plurality of anterior and posterior lens shapes to achieve the required optical performance.

In an exemplary embodiment, the device may have a lens that is constructed with at least one rigid lens shape on the optic axis that are displaced by the outer edges that separate and move apart, or come close together as the capsule is broadened or pinched together during accommodation or unaccommodation.

In an exemplary embodiment, the device may have a lens that is shaped with an outer rim and attachment feature that controls the spherical shape of the lens at various diopters.

In an exemplary embodiment, the device may have a haptic portion of the device has a rim stiffness equal to or greater than the optic to provide the necessary force to deform or pull radially on the lens and maintain a spherical lens shape during accommodation.

In an exemplary embodiment, the device may have an integrated, one piece haptic.

In an exemplary embodiment, the device may have a haptic having a shape that allows for axially movement about the lens by using rolling rotation, pivoting, offsetting at the connection to the haptic.

In an exemplary embodiment, the device may have a haptic that is shaped to control the force applied to the lens while providing a compatible biomechanical interaction with the ciliary muscle of the human eye and its natural accommodative control system.

In an exemplary embodiment, the device may have a haptic shape that may dictate optic attachment and control the optic position posteriorly and anteriorly relative to the haptic actuating rim of the device.

In an exemplary embodiment, the device may have a haptic portion that forms a limiting boundary to resist growth of posterior capsule opacification (pco) cells with a shape that provides a continuous rim near the equator.

In an exemplary embodiment, the device may have a lens coupled to an outer frame (haptic), the radial movement of the outer equatorial surface of the haptic adjustably changes the shape and thickness of the lens.

In an exemplary embodiment, the device may have a lens that is foldable or injectable for delivery into the eye.

The present invention advantageously provides a haptic rim with a feature of a continuous ring edge to prevent PCO by blocking cell growth from the capsule equator to the posterior optic zone of the posterior capsule.

The present invention will be able to provide a stable lens replacement with similar forces and displacements as are naturally available in the human, biomechanical accommodative system that is thereby biocompatible.

As the brain senses the need to focus on a near object, the ciliary muscle contracts, thereby changing/reducing tension on the peripheral zonules attached to the lens capsule. For near vision this accommodated shape change results in a smaller overall capsule diameter with an associated thicker axial crossection that can be utilized to control the actuating lens haptic shape which allows the lens implant herein described to relax into a smaller more spherical overall shape with smaller anterior and posterior lens optical radii. An accommodated, higher diopter lens is thereby obtained, which is thicker in the center for close vision with a reduced lens circumference at the equator. For far vision the opposite occurs, yielding a thinner lens center with an increased lens circumference at the equator.

Another advantage of the present invention is providing an accommodating intraocular lens that may be comprised of at least one lens to achieve the desired optic change.

In yet another advantage of the present invention, the present invention may provide an accommodating intraocular lens that may be comprised of a plurality of lenses to achieve the desired optic changes.

An advantage of the present invention is to provide an AIOL that may have a fixed optic and a flexible optic acting in conjunction wherein the fixed optic and/or the flexible optic maybe implanted subsequent to each respective optic.

Still another advantage of the present invention is to provide an AIOL that may have a plurality of haptics that may contract in response to natural response to ciliary muscles on the haptic.

Yet another advantage of the present invention is to provide an AIOL that may have no haptic yet still allow for movement of the lens in response to muscle contraction and relaxation.

In still another exemplary embodiment of the present invention, an AIOL may be provided having a simple bladder shape that contacts the eye capsule in which case a posterior capsulotomy may be required to remove the affect of posterior capsule opacification due to membrane growth.

Another advantage of the present invention is to provide an AIOL that may have an anterior and posterior shape that may be optimized to control flexing and counteracting of optic ray focusing.

Additionally, an advantage of the present invention is to provide an AIOL that may have an anterior and posterior portion wherein the anterior cross section affects the posterior and the sum of the two surfaces may allow for flexing of the lens and focus by the patients utilizing the AIOL.

Yet another exemplary embodiment of the present invention is an AIOL having a double lens wherein two lenses may be positioned in proximity to each other and each counteracts the others flex and focus.

Still another advantage of the present invention is to provide an AIOL having a lens with index matching fluid wherein the AIOL may have either one lens or a plurality of lenses.

An advantage of the present invention is to provide an AIOL that utilizes muscle action on zonules and capsules to manipulate the haptic of the AIOL.

In still another exemplary embodiment, an AIOL is provided that may allow for force applied to the device to act on the lens without the need to actually contact the lens directly.

In a exemplary embodiment of the invention, an AIOL may he provided wherein force applied to the haptic portion of the device may allow for curvature of the lens in response to the applied force.

Another object of the present invention is to provide an AIOL that may control the optical ray tracing affect while light is transmitted and/or refracted through the flexing lens.

Another exemplary embodiment of the present invention is to provide an AIOL that may use leverage to magnify the force on the lens from muscle contractions on zonules and capsules.

In yet another exemplary embodiment of the present invention is to provide an AIOL wherein the AIOL may have a singular lens yet may have two different stiffness modulus.

Still a further exemplary embodiment of the present invention is to provide an AIOL wherein the AIOL may have a singular lens having differing stiffness modules wherein the pullers may be stiffer than the softer lens which may yield more lens shape changes in response to muscle exertion on the AIOL.

Another exemplary embodiment of the present invention is to provide an AIOL wherein the AIOL may utilize a soft lens core with a thin skin covering the core.

Yet another exemplary embodiment of the present invention is to provide an AIOL wherein the shape of the lens may provide differing adjustments for near vision and far vision patients.

Still another exemplary embodiment of the present invention is to provide an AIOL wherein the shape of the lens may be accommodated and/or may be un-accommodated.

In an exemplary embodiment of the present invention, an AIOL may be provided wherein the AIOL may have a plurality of haptics.

Yet another exemplary embodiment of the present invention is to provide an AIOL wherein the AIOL may have a singular haptic for movement of the lens in response to the haptic.

In another exemplary embodiment of the present invention, an AIOL is provided wherein the AIOL may have a relatively hardened haptic which may be utilized in un-accommodated intraocular lenses and a stiff yet softer haptic which may be utilized in an accommodating intraocular lens wherein the stiff yet softer haptic may be contracted wherein the contraction of the haptic may allow for movement of the lens relative to that haptic.

Another exemplary embodiment of the present invention is providing an AIOL having multiple lens configurations wherein the lens may have a flexible membrane to allow volume change between a plurality of lens surfaces.

Yet another exemplary embodiment of the present invention is to provide an AIOL wherein the lens surface may be integrally connected with a second lens portion to allow for increased flexibility and structural cooperation between the lenses.

Still another exemplary embodiment of the present invention is to provide an AIOL wherein the lens may be configured in a plurality of different shapes based on patient need.

These and other objects of the invention will become more clear when one reads the following specification, taken together with the drawings that are coupled hereto. The scope of protection sought by the inventors may be gleaned from a fair reading of the Claims that conclude this specification.

Additional features and advantages of the present invention are described in, and will be apparent from, the detailed description of the presently preferred embodiments and from the drawings.

BRIEF DESCRIPTION OF THE DRAWING AND ATTACHMENTS

The invention and its various embodiments can now be better understood by turning to the following detailed description of the preferred embodiments, which are presented as illustrated examples of the invention defined in the claims. It is expressly understood tat the invention as defined by the claims may be broader than the illustrated embodiments described below.

DETAILED DESCRIPTION OF THE PREFERRED EMBODIMENT

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed herein even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims therefore include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Thus, the detailed description set forth below in connection with the appended drawings is intended as a description of the presently preferred embodiments of the invention and is not intended to represent the only forms in which the present invention may be constructed or utilized. The description sets forth the functions and the sequence of steps for constructing and operating the invention in connection with the illustrated embodiments. It is to be understood, however that the same or equivalent functions may be accomplished by different embodiments that are also intended to be encompassed within the spirit of the invention.

Figure 1:
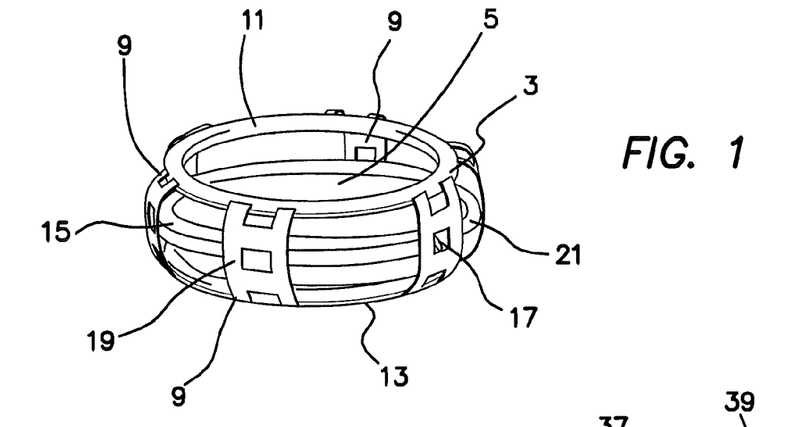
FIG. 1 illustrates a front perspective view of the invention including the lens portion and the haptic portion in an exemplary embodiment of the present invention.

As illustrated in FIG. 1, the present invention improves upon the prior art intraocular lens by providing a flexible optic 1 controlled by forces from the novel haptic 3 design that will result in a higher diopter change during accommodation, when the AIOL presented herein is compared with a vaulting AIOL. The lens 5, herein described, can advantageously displace axially to still allow the natural benefits of an axially vaulting lens 5 as well.

As illustrated in FIG. 1, the flexible optic 1 may have a plurality of parts wherein the lens 5 is enclosed about a haptic 3. The haptic 3 may have a plurality of ribs 9 extending from a top portion 11 of the haptic 3 to a bottom portion 13 of the haptic 3. The rib 9 extends from this top portion 11 to the bottom portion 13. The lens 5 may be contained within the haptic 3. In an exemplary embodiment of the present invention, the lens 5 may be detachably connected to the haptic 3 using a connection means 15. In an embodiment, the connection means 15 may be a slot 17 contained in the midportion 19 of the haptic 3 wherein the slot 17 is designed to facilitate engagement of an outside edge 21 of the lens 5. The haptic 3 may be molded integrally to the lens with a different (high stiffness) material than the lens.

In an exemplary embodiment of the present invention, the haptic 3 may be constructed of a resilient material allowing for the haptic 3 to retain rigidity, yet still allow for compression of the haptic 3 to facilitate curvature of the lens 5. In an embodiment, the haptic 3 may be constructed of synthetic material which is further explained below. However, it should be understood that the haptic 3 may be constructed of any suitable material to allow for structural rigidity yet still accommodate flexion.

Figure 5:
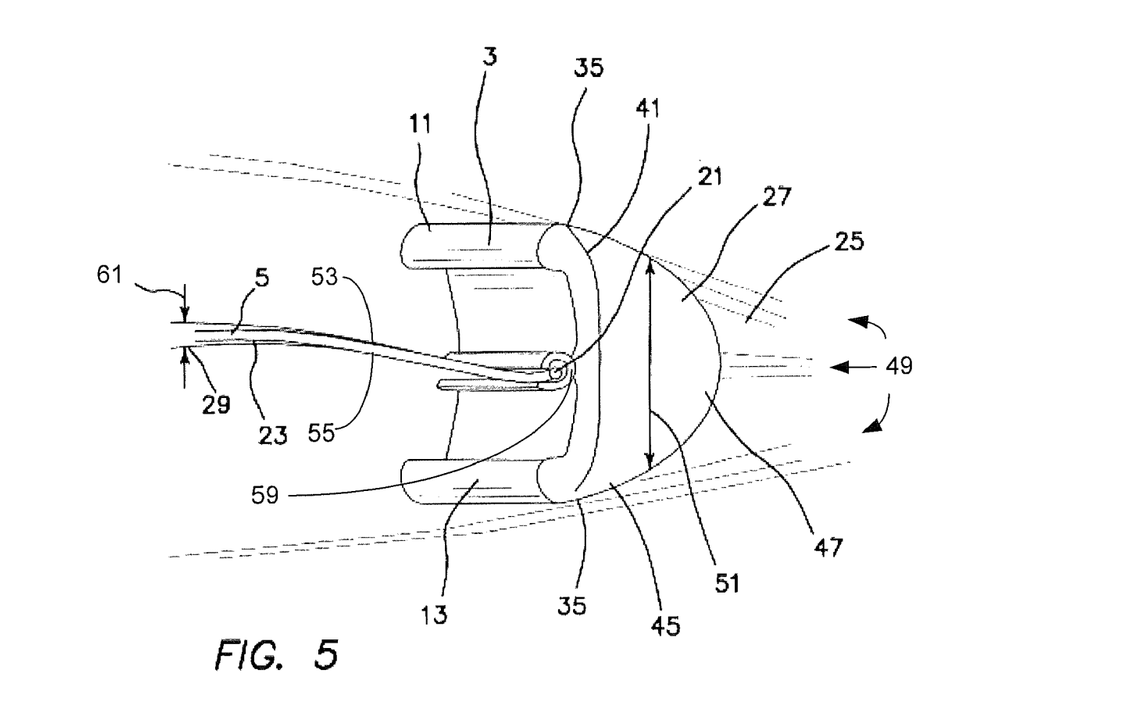
FIG. 5 illustrates another front cross-sectional perspective view of the present invention illustrating the device in association with ciliary muscles in the eye.

FIG. 1 further illustrates a conforming lens 5 with a separate actuating haptic 3. As the eye needs to accommodate for near vision, the optic or lens 5 is allowed to return to its relaxed radial position with a smaller anterior and posterior optical radii, in the natural capsular bag of the eye (not shown) while maintaining a spherical or otherwise beneficial or custom optical shape. The lens curvature 23 may be decreased to a smaller radii in response to forces applied when ciliary muscle 25 tightens thereby reducing the inside diameter of the muscle radially at the capsule equators, further resulting in axially broadening of the capsule surface 27 as illustrated in FIG. 5. The tightening of the cilicary muscle onto the capsule 27 surface ultimately reduces zonule tension at the edges of the capsule surface 27 relaxing the haptic 3 to its normally relaxed position radially inward at the equator, and consequently allowing the outside edge 21 of the lens 5 to move inward. This allows the lens 5 to assume its naturally relaxed smaller anterior and posterior radii with a thicker lens 5 center 29. When the eye (not shown) needs to un-accommodate for distance vision, the lens 5 may be stretched radially, or flattened, in the natural capsular bag of the eye (not shown) while maintaining a spherical optical shape. The lens curvature 23 changes or flattens in response to forces applied when ciliary muscle 25 relaxation further results in axial compression of the capsule 27 as the zonules (49) ultimately pinch the edges 35 of the capsule surface 27 bending the haptic 3 in that location radially outward at the equator, which consequently pulls the outside edge 21 of the lens 5 outward decreasing capsule depth 51.

Figure 2:
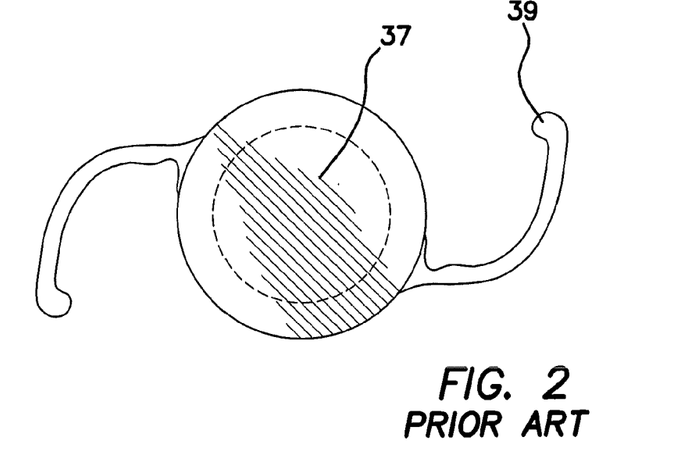
FIG. 2 illustrates a prior art intraocular cataract lens including the haptic portion and the lens portion.
Figure 3:
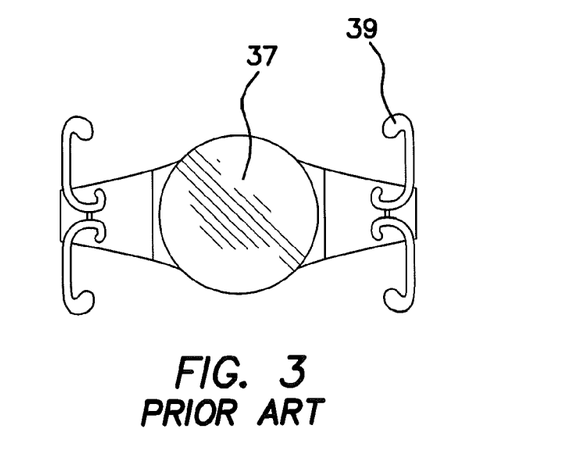
FIG. 3 illustrates another prior art intraocular device including the haptic portion and the lens portion that allows for displacement of the fixed optics.

FIGS. 2 and 3 illustrate prior art Intraocular lenses wherein the prior art discloses a lens 37 and a haptic 39. However, a problem with the prior art lenses is that they are primarily fixed optic lens 37 apparatuses. The lens 37 in FIG. 2, whether plain or with gradient freznel optics, cannot move when the eye needs to adjust to closer objects and the like. FIG. 3 illustrates a forward moving lens 37 wherein the lens 37 may move forward a certain amount with movement of the haptic 39. However, the problem with the prior art Intraocular lens is that the diopter correction is too small to affect real correction of a patients vision in need of more visual adaption for seeing far and/or near objects.

Figure 4:
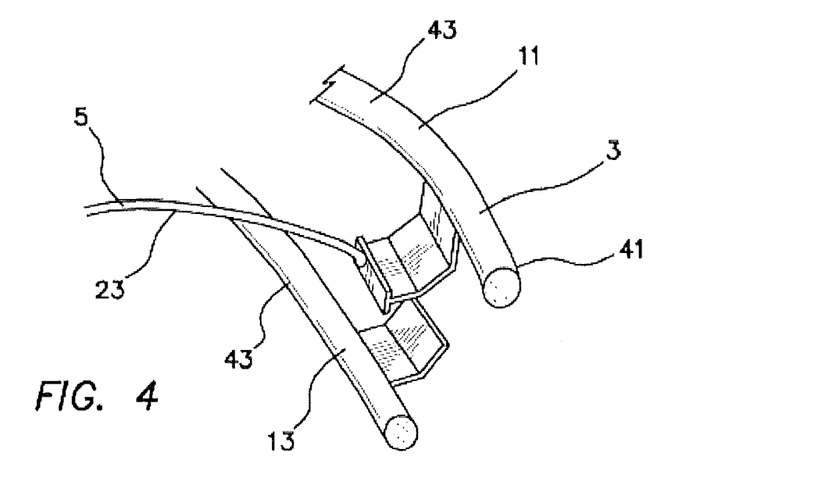
FIG. 4 illustrates a front cross-sectional perspective view of the present invention illustrating the connection of the lens to the haptic.

As further illustrated in FIG. 4, the present invention advantageously may have a haptic rim 41 with a feature of a continuous ring edge 43 to prevent PCO by blocking cell growth from the capsule equator to the posterior optic zone 45 of the posterior capsule surface 47 which is further illustrated in FIG. 5.

Further illustrated in FIG. 5 is the flexible optic device 1 implanted in the capsule 27 of the eye (not shown). The device 1 will be able to provide a stable lens 5 replacement with similar forces and displacements as are naturally available in the human, biomechanical accommodative system that is thereby biocompatible. As the brain senses the need to focus on a near object (not shown), the ciliary muscle 25 contracts radially, thereby changing/reducing tension on the peripheral zonules 49 attached to the lens capsule 27. For near vision this accommodated shape change results in a smaller overall capsule diameter with an associated thicker axial crossection that can be utilized to control the actuating lens haptic 3 shape which may allow the lens 5 implant to relax into a smaller more spherical overall shape with smaller anterior 53 and posterior 55 lens optical radii. An accommodated, higher diopter lens is thereby obtained which is thicker in the center for close vision with a reduced lens circumference at the equator 21. For far vision the opposite occurs, yielding a thinner lens center 29 with an increased lens circumference at the equator 21.

FIG. 5 illustrates the manipulation of the AIOL device 1. As the eye (not shown) unaccommodates, the haptic 3 of this AIOL device 1 is compressed closer together, in the axial direction as the attachment of the anterior and posterior zonules 49 to the capsule 27 are displaced outwardly in the radial direction. This occurs because the zonules 49 are normally spread apart axially when accommodated, providing a thicker natural lens capsule, or straighter AIOL haptic 3 with a smaller equatorial diameter. The lens 5 is normally relaxed in this accommodated position, and the zonules 49, in general, converge as they propagate radially outward to attach to the tightened ciliary muscle 25. When the ciliary muscle 25 relaxes during unaccommodation, the equator of the natural lens or the equator 59 of the AIOL haptic 3 is displaced radially outward. This causes the anterior and posterior zonules 49 to come closer together where they attach to the capsule as the ciliary muscle 25 diameter increases, thereby pinching or compressing the capsule 27 axially which also compresses and curves the AIOL haptic 3. This added curvature to the haptic 3 displaces the equator 49 of the haptic 3 radially outward, which alternately pulls the softer lens rim 61 and lens 5 itself to a more flattened shape with a larger optical radius for distance vision.

In an exemplary embodiment of the present invention, the device 1 may employ a plurality of different shapes, construction, and material properties of the lens 5 and haptic 3 features, and may provide a plurality of lenses.

It is generally contemplated that the AIOL can be made of suitable materials compatible with the human eye. Such materials include natural and synthetic polymers (e.g., silicone or many other materials in this category that could even be specially formulated to meet the design requirements), various metals and metal alloys, naturally occurring materials, textile fibers, hydro-gel materials, and all reasonable combinations thereof.

Figure 7:
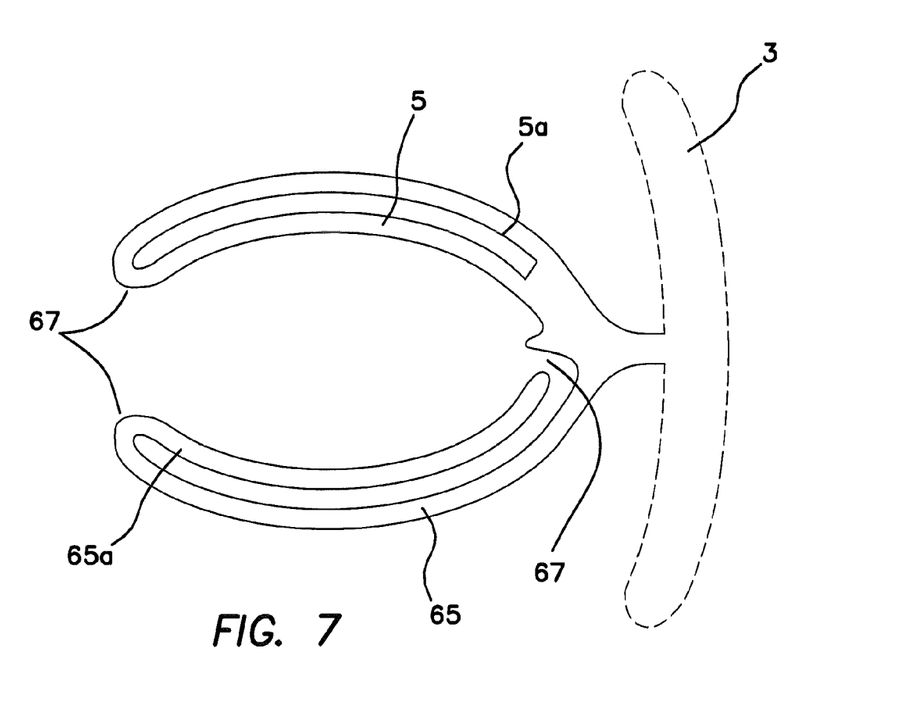
FIG. 7 illustrates a front view of another exemplary embodiment of the present invention.
Figure 8:
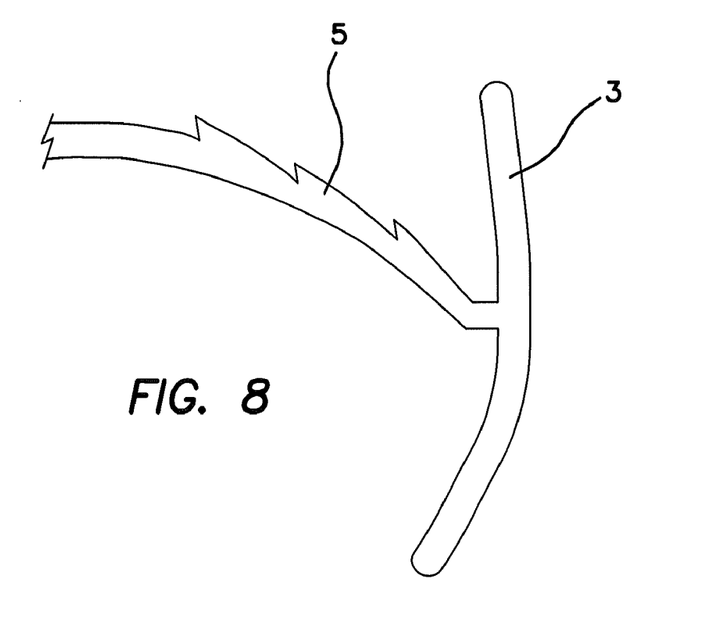
FIG. 8 illustrates a front view of yet another exemplary configuration of the present invention.
Figure 9:
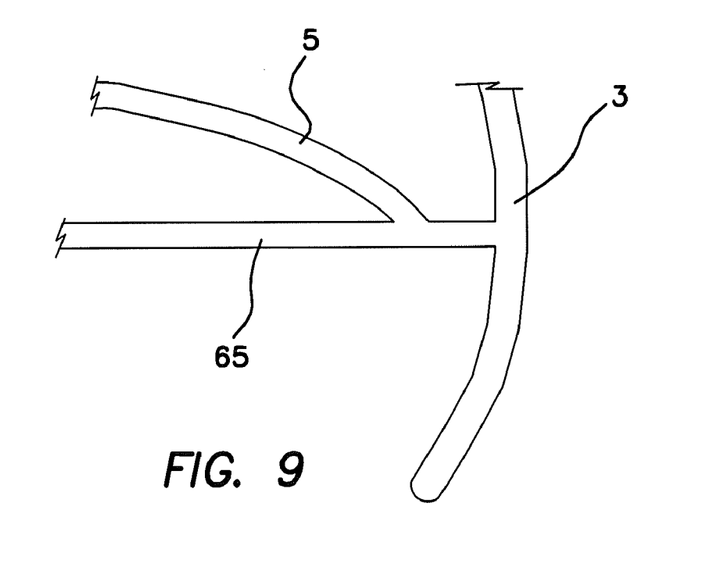
FIG. 9 illustrates a front view of still another exemplary configuration of the present invention.

FIGS. 7-9 illustrate alternative lens 5 and haptic 3 configurations. FIG. 7 illustrates an exemplary lens 5 shape wherein the device I may employ a single or dual lens configuration having a first lens radius $5a$ and a second lens radius $65a$. Both lens radii $5a$, $65a$ may be connected to the haptic 3 and may further contain fluid vents 67 thereon as illustrated in FIG. 7. Lens raddi $5a$, $65a$ may affect material thickness, and may he designed to maintain sphericity of the lens outer shape. Additionally, the shape of the dual lens may be configured to that illustrated in FIG. 9 wherein the second lens 65 is substantially flat and the first lens 5 has a generally curved surface.

Figure 6:
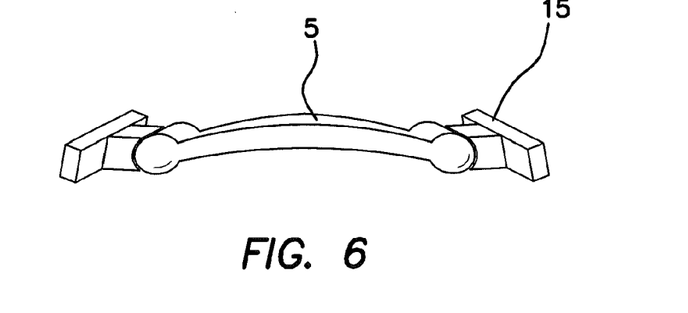
FIG. 6 illustrates a front view of the lens portion of the device in an exemplary embodiment of the present invention.

FIG. 6 illustrates the lens 5 and its connection means 15 whereby the connection means may be permanently and/or detachably connected to the haptic 3. FIG. 4 further illustrates the connection of the lens 5 to the haptic 3. As illustrated, the connection means 15 of the lens 5 may attached to a connection portion 69 of the haptic 3 whereby the lens 5 movement is manipulated by movement of the haptic 3. Additionally, it should be understood that the lens 5 may have a convex surface. However, the surface of the lens 5 may have a plurality of shapes to facilitate proper diopter correction by a patient and for proper placement within the haptic 3 as illustrated in FIGS. 8 and 9.

Thus, specific embodiments and applications of accommodative intraocular lens have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . , and N, the text should be interpreted as requiring only one element from the group, not A plus N, or B plus N, etc.

The invention claimed is:

1. An accommodating intraocular lens comprising:
a conforming lens for insertion into the capsular bag of the eye;
an actuating haptic having a haptic rim with a feature of a continuous ring edge wherein the conforming lens is detachably connected to the actuating haptic;
a second lens connected to the actuating haptic; and
the haptic having a plurality of ribs extending from a top portion of the haptic to a bottom portion of the haptic whereby the top portion is separated from the bottom portion of the haptic by the plurality of ribs extending from the top portion of the haptic to the bottom portion of the haptic and further wherein the conforming lens is contained between the top portion of the haptic and the bottom portion of the haptic and radially within the haptic.

2. The accommodating intraocular lens of claim 1, wherein the conforming lens is solid and thin, with a thin surface film filled with a soft inner core.

3. The accommodating intraocular lens of claim 1, wherein the conforming lens has an interior that is a solid.

4. The accommodating intraocular lens of claim 1, wherein the conforming lens has an interior portion wherein the interior portion is liquid.

5. The accommodating intraocular lens of claim 1, wherein the conforming lens has an interior portion wherein the interior portion is filled with a gaseous solution.

6. The accommodating intraocular lens of claim 1, wherein the conforming lens is convexed anteriorly with a planar posterior surface.

7. The accommodating intraocular lens of claim 1, wherein the conforming lens is made up of a plurality of anterior and posterior lens shapes to achieve the required optical performance.

8. The accommodating intraocular lens of claim 1, wherein the conforming lens is constructed with at least one rigid lens shape on the optic axis that are displaced by outer edges of the conforming lens that separate and move apart, or come close together as the capsule is broadened or pinched together during accommodation or un-accommodation.

9. The accommodating intraocular lens of claim 1, wherein the conforming lens is shaped with an outer radius and inner curvature that controls the spherical shape of the lens at various diopters.

10. The accommodating intraocular lens of claim 1 wherein the conforming lens is shaped with an outer radius, inner curvature and an attachment feature that controls the spherical shape of the lens at various diopters.

11. The accommodating intraocular lens of claim 1, wherein the haptic portion of the device has a rim stiffness equal to or greater than the optic to provide the necessary force to deform or pull radially on the conforming lens and maintain a spherical lens shape during accommodation.

12. The accommodating intraocular lens of claim 1, wherein the haptic shape moves axially about the conforming lens by using rolling rotation, pivoting, offsetting at the connection to the haptic.

13. The accommodating intraocular lens of claim 1, wherein the haptic is shaped to control the force applied to the conforming lens while providing a compatible biomechanical interaction with the ciliary muscle of the human eye and its natural accommodative control system.

14. The accommodating intraocular lens of claim 1, wherein the haptic shape dictates optic attachment and controls the optic position posteriorly and anteriorly relative to a haptic actuating rim of the device.

15. The accommodating intraocular lens of claim 1, wherein the haptic portion of the device forms a limiting boundary to resist growth of posterior capsule opacification (pco) cells with a shape that provides a continuous rim near the equator.

16. The accommodating intraocular lens of claim 1, wherein the conforming lens is coupled to an outer frame of the haptic, the movement of an outer surface of the haptic adjustably changes the shape and thickness of the conforming lens.

17. The accommodating intraocular lens of claim 1, wherein the conforming lens is foldable or injectable for delivery into the eye.

18. The accommodating intraocular lens of claim 1, wherein the conforming lens comprises a curved surface and the second lens comprises a substantially flat surface.

19. The accommodating intraocular lens of claim 1, further comprising a fluid vent on a surface of the conforming lens.

\* \* \* \* \*